(12) United States Patent
Jogasaki (10) Patent No.: US 11,130,244 B2
(45) Date of Patent: Sep. 28, 2021

(54) BENDING MECHANISM AND FLEXIBLE MEDICAL APPARATUS

(71) Applicant: OLYMPUS CORPORATION, Tokyo (JP)

(72) Inventor: Shuya Jogasaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1116 days.

(21) Appl. No.: 15/481,616

(22) Filed: Apr. 7, 2017

(65) Prior Publication Data

US 2017/0210015 A1 Jul. 27, 2017

Related U.S. Application Data

(63) Continuation of application No. PCT/JP2014/077954, filed on Oct. 21, 2014.

(51) Int. Cl.
| | |
|---|---|
| *A61B 1/01* | (2006.01) |
| *B25J 17/00* | (2006.01) |
| *B25J 18/06* | (2006.01) |

(52) U.S. Cl.
CPC .......... *B25J 17/00* (2013.01); *A61B 1/01* (2013.01); *B25J 18/06* (2013.01)

(58) Field of Classification Search
CPC ...... F16C 1/02; F16C 1/04; F16C 1/06; F16C 1/101; F16C 1/106; F16C 1/22; F16C 1/223; F16C 1/265; B25J 17/00; B25J 18/06; A61B 1/01

See application file for complete search history.

(56) References Cited

U.S. PATENT DOCUMENTS

| | | | |
|---|---|---|---|
| 4,765,795 A | 8/1988 | Rebman | |
| 8,613,230 B2 * | 12/2013 | Blumenkranz | .... A61B 17/3462 |
| | | | 73/862.044 |
| 2008/0257096 A1 | 10/2008 | Zhu et al. | |
| 2008/0269558 A1 | 10/2008 | Yahagi et al. | |

(Continued)

FOREIGN PATENT DOCUMENTS

| | | |
|---|---|---|
| JP | S62-292385 A | 12/1987 |
| JP | 2005-271183 A | 10/2005 |

(Continued)

OTHER PUBLICATIONS

Japanese Office Action dated Feb. 5, 2019 in Japanese Patent Application No. 2016-554977.

(Continued)

*Primary Examiner* — Jake Cook
*Assistant Examiner* — T. Scott Fix
(74) *Attorney, Agent, or Firm* — Scully, Scott, Murphy & Presser, P.C.

(57) ABSTRACT

In order to prevent swiveling of unintended joint pieces and enhance positioning and motion reproducibility of a distal end portion, a bending mechanism includes: a plurality of joint pieces connected in series along the longitudinal axis; a plurality of elongated tension-transmissions that transmit tensions for individually driving the joint pieces; and at least one guide having guide channels that movably support the tension-transmissions in the longitudinal direction thereof and that guide the tension-transmissions along curved paths extending around the longitudinal axis.

20 Claims, 9 Drawing Sheets

(56) References Cited

U.S. PATENT DOCUMENTS

| | | | |
|---|---|---|---|
| 2008/0302200 A1* | 12/2008 | Tobey | B25J 13/084 74/490.02 |
| 2009/0012648 A1* | 1/2009 | Buckingham | B25J 18/06 700/260 |
| 2009/0095112 A1* | 4/2009 | Buckingham | B25J 18/06 74/490.05 |
| 2009/0099420 A1 | 4/2009 | Woodley et al. | |
| 2010/0217082 A1 | 8/2010 | Ito et al. | |
| 2010/0234988 A1* | 9/2010 | Buckingham | B25J 18/06 700/245 |
| 2010/0236352 A1 | 9/2010 | Iida | |
| 2013/0312564 A1* | 11/2013 | Kim | B25J 18/06 74/490.04 |
| 2015/0141756 A1* | 5/2015 | Cheng | A61B 1/0016 600/146 |
| 2015/0352728 A1* | 12/2015 | Wang | A61B 1/00 74/490.04 |
| 2016/0151908 A1 | 6/2016 | Woodley et al. | |

FOREIGN PATENT DOCUMENTS

| | | |
|---|---|---|
| JP | 2008-272204 A | 11/2008 |
| JP | 2009-119064 A | 6/2009 |
| JP | 2010-223724 A | 10/2010 |
| JP | 2012-096337 A | 5/2012 |
| WO | WO 2007/069667 A1 | 6/2007 |
| WO | 2009/048796 A2 | 4/2009 |

OTHER PUBLICATIONS

International Search Report dated Jan. 20, 2015 issued in PCT/JP2014/077954.

* cited by examiner

BENDING MECHANISM AND FLEXIBLE MEDICAL APPARATUS

CROSS-REFERENCE TO RELATED APPLICATIONS

This is a continuation of International Application PCT/JP2014/077954, with an international filing date of Oct. 21, 2014, which is hereby incorporated by reference herein in its entirety. This application claims the benefit of International Application PCT/JP2014/077954.

TECHNICAL FIELD

The present invention relates to a bending mechanism and a flexible medical apparatus.

BACKGROUND ART

There is a known endoscope having a bending mechanism incorporated in a cover, wherein the bending mechanism is configured of a plurality of joint pieces swivelably connected to one another to form an elongated shape and the swiveling of the joint pieces is controlled via a tension applied to wires that are guided in a substantially straight line along the longitudinal axis direction and connected to the joint pieces (refer to, for example, Patent Literature 1 below).

CITATION LIST

Patent Literature

{PTL 1}
Japanese Unexamined Patent Application, Publication No. 2009-119064

SUMMARY OF INVENTION

Technical Problem

An object of the present invention is to provide a bending mechanism and a flexible medical apparatus capable of enhancing positioning and motion reproducibility of the distal end portion by preventing swiveling of unintended joint pieces.

Solution to Problem

One aspect of the present invention is a bending mechanism including: a plurality of bending joints connected in series along a longitudinal axis; a plurality of elongated tension-transmissions that transmit tensions for individually driving the bending joints; and at least one guide having guide channels that movably support the tension-transmissions in the longitudinal direction thereof and that guide the tension-transmissions along curved paths extending around the longitudinal axis.

In the above-described aspect, the guide may be a planar guide plate disposed so as to intersect the longitudinal axis, and the guide channels may be through-holes or through-grooves that pass through the guide plate in a plate-thickness direction.

In the above-described aspect, the guide plate may be attached such that the angle thereof can be adjusted about the longitudinal axis.

In the above-described aspect, the guide plate may have, radially inward from the through-holes or the through-grooves, an opening that passes therethrough in the plate-thickness direction.

In the above-described aspect, the guide plate may include: a first plate part provided such that the angle thereof can be adjusted about the longitudinal axis relative to one of the bending joints; and a second plate part attached such that the angle thereof can be adjusted about the longitudinal axis relative to the first plate part, the opening may be provided in the first plate part, and the guide channels may be provided in the second plate part.

In the above-described aspect, the guide channels may be formed so as to be angled towards a circumferential direction relative to a direction parallel to the longitudinal axis.

In the above-described aspect, the tension-transmissions may be wires covered with sheaths.

In the above-described aspect, the surfaces of the sheaths and the inner walls of the guide channels may be composed of different materials.

In the above-described aspect, a coating for decreasing the friction with the inner walls of the guide channels may be applied to the surfaces of the sheaths.

Another aspect of the present invention is a flexible medical apparatus including: one of the above-described bending mechanisms; and a flexible tubular outer sheath covering the outer circumference of the bending mechanism.

DESCRIPTION OF EMBODIMENTS

A flexible medical apparatus 1 and a bending mechanism 2 according to one embodiment of the present invention will now be described with reference to the drawings.

Figure 1:
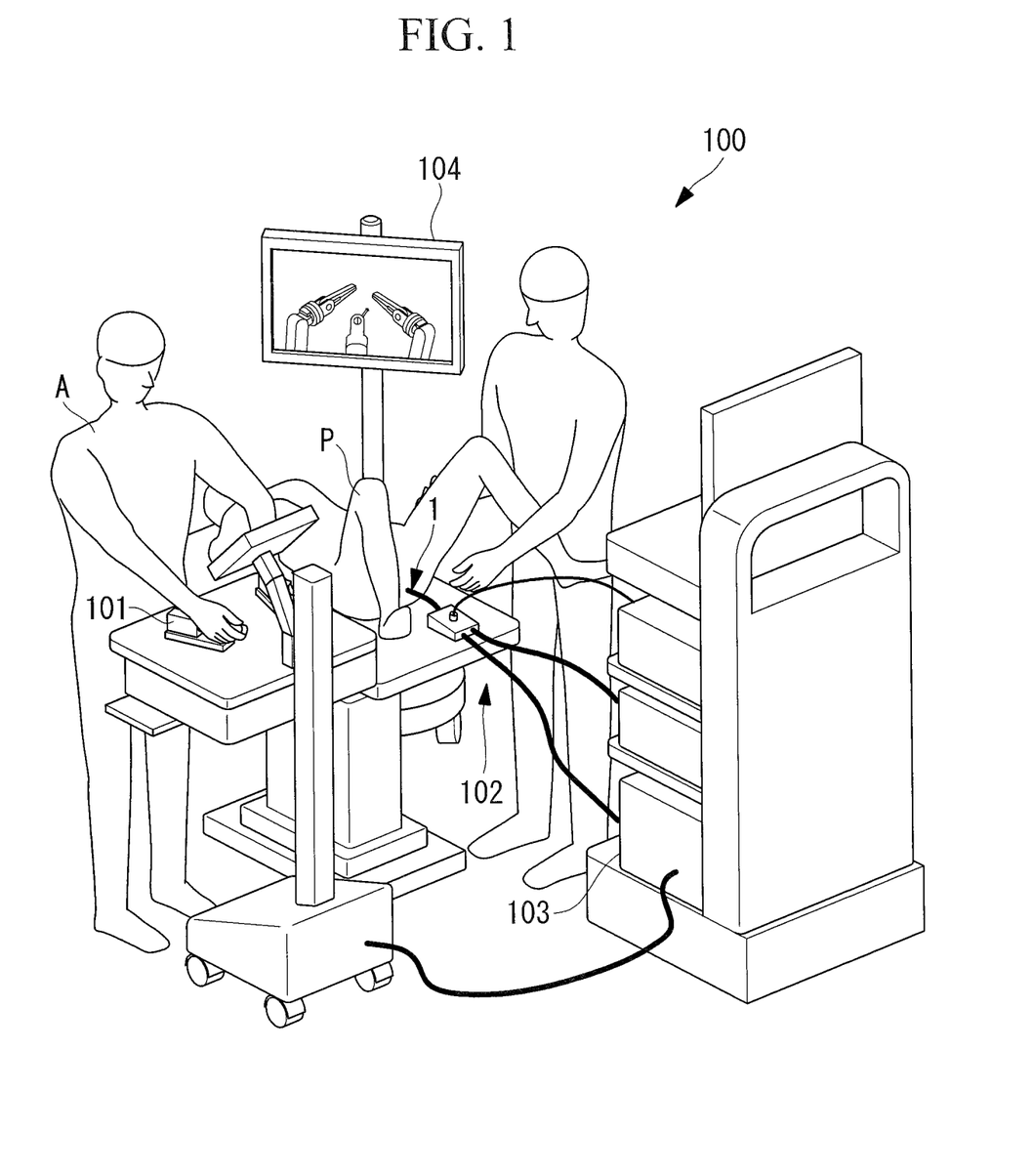
FIG. 1 is an overall configuration diagram depicting a medical system including a flexible medical apparatus according to one embodiment of the present invention.

The flexible medical apparatus 1 according to this embodiment is applied to, for example, a medical system 100 shown in FIG. 1.

This medical system 100 includes: a master device 101 operated by a physician A; a slave device 102 driven according to an input via the master device 101; a controller 103 for controlling the slave device 102 on the basis of the input to the master device 101; and a monitor 104. The slave device 102 includes an insertion section to be inserted into the body cavity of a patient P and also includes the flexible medical apparatus 1 according to this embodiment at a distal end of that insertion section.

Figure 2:
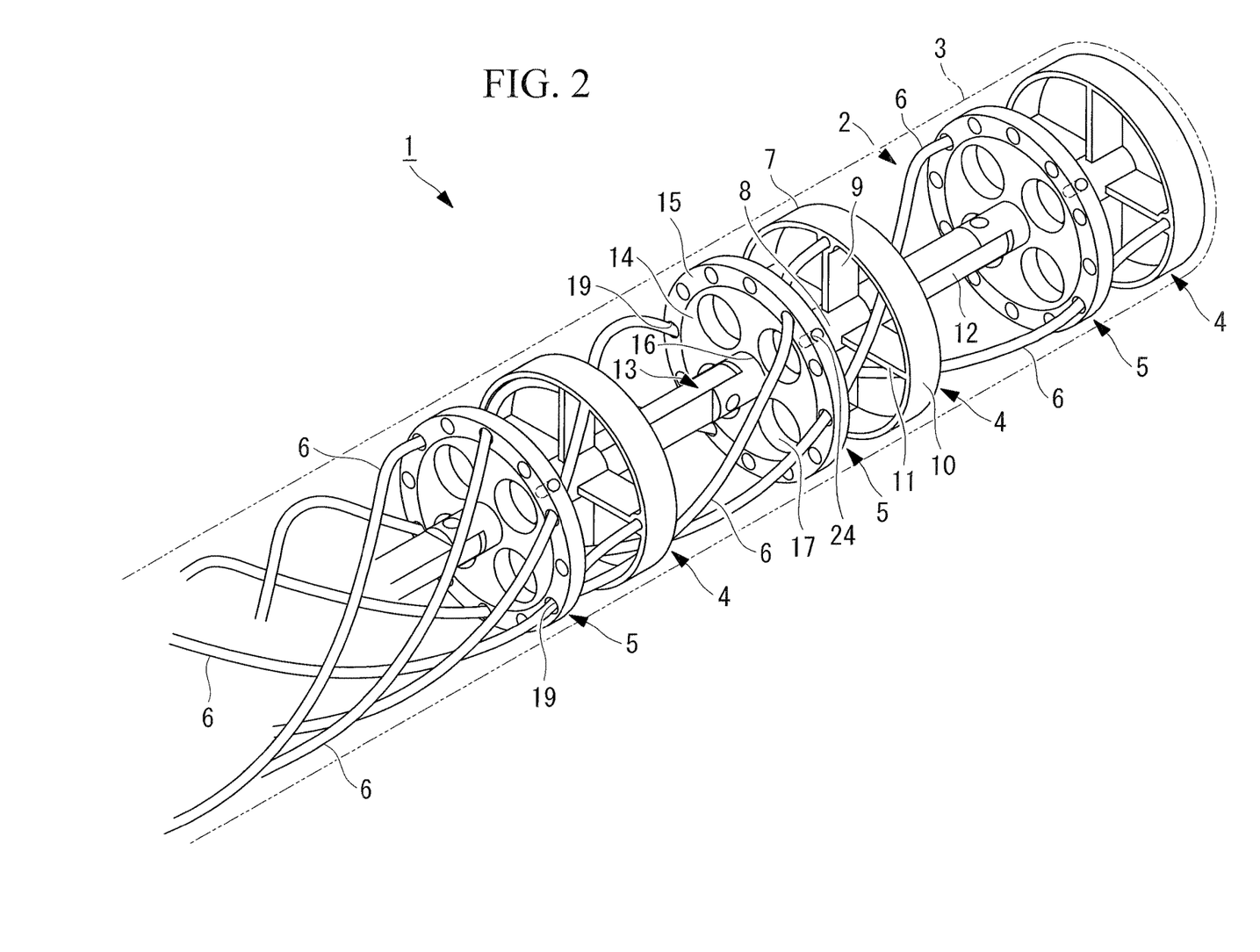
FIG. 2 is a perspective view of a distal end section, depicting a bending mechanism and a flexible medical apparatus according to one embodiment of the present invention.

As shown in FIG. 2, the flexible medical apparatus 1 according to this embodiment includes the bending mechanism 2 and an outer sheath 3 formed of a flexible material that covers the external surface of the bending mechanism 2.

As shown in FIG. 2, the bending mechanism 2 according to this embodiment includes: a plurality of joint pieces connected in series (bending joints) 4; a guide plate (guide) 5 attached to each of the joint pieces 4; and tension-transmissions 6 that pass through the guide plates 5 and the joint pieces 4, one end of each of the tension-transmissions 6 being connected to one of the joint pieces 4.

Figure 3:
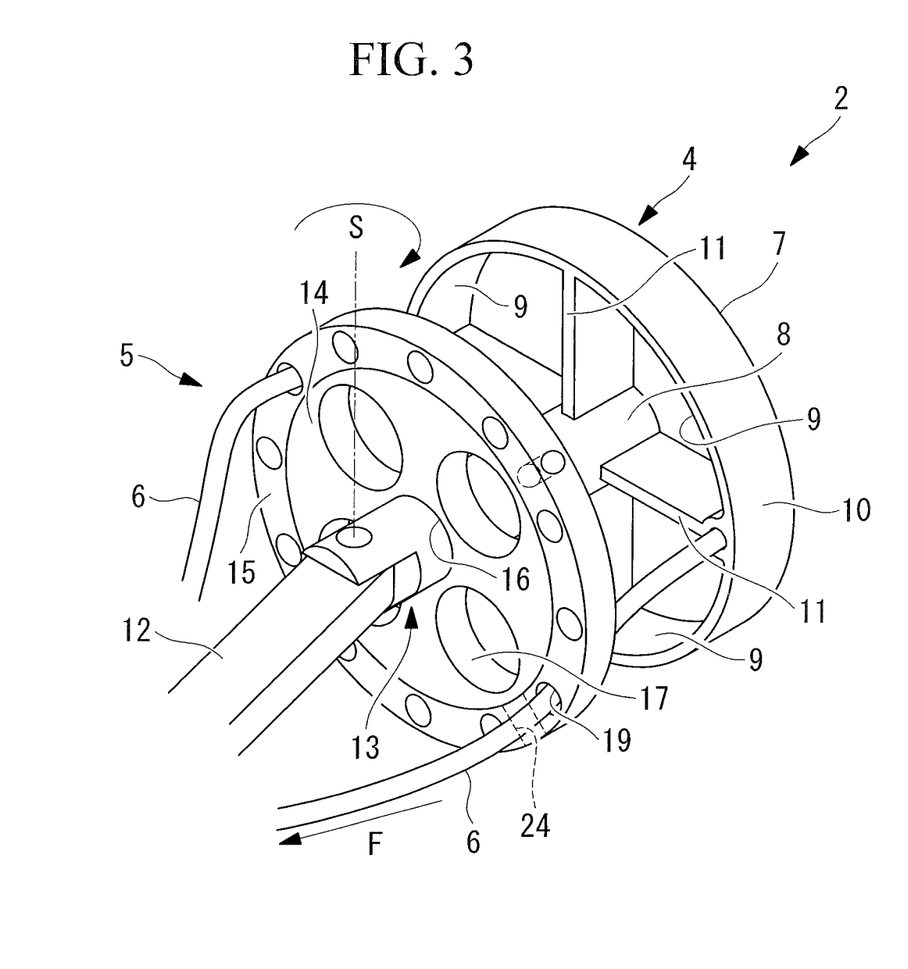
FIG. 3 is a perspective view depicting a distal end section of the bending mechanism in FIG. 2.

As shown in FIG. 3, the joint pieces 4 each include: a disc-shaped body part 7 and a first columnar part 8 extending in one direction along the axis line at the center of that body part 7. The body part 7 has four through-holes 9 passing therethrough in the thickness direction and is configured such that the first columnar part 8 at the enter thereof and a ring-shaped part 10 on the outer circumference of the body part 7 are connected via four spokes 11. In this manner, each of the through-holes 9 is formed as a space surrounded by the ring-shaped part 10, the first columnar part 8, and two neighboring spokes 11.

Figure 4:
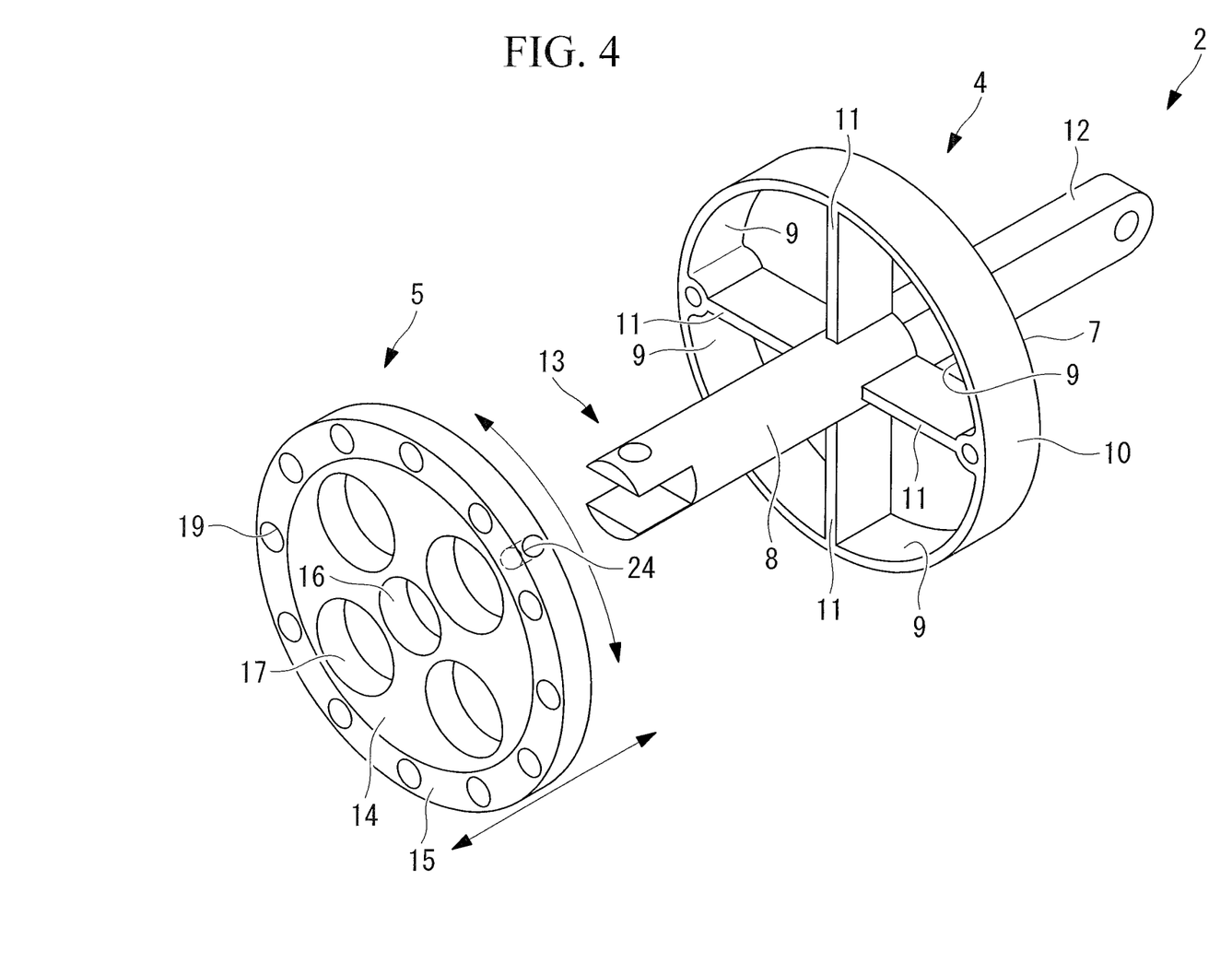
FIG. 4 is an exploded perspective view depicting a joint piece and a guide plate in the middle of the bending mechanism in FIG. 2.

As shown in FIG. 4, the joint pieces 4 other than the joint piece 4 provided at the most distal end each include a second columnar part 12 that extends along the axis line in the opposite direction of the body part 7 from the first columnar part 8. The first columnar part 8 has, at the basal end thereof, a linkage section 13 that is swivelably connected to the distal end of the second columnar part 12 provided on the neighboring joint piece 4. In the example shown in FIGS. 2 to 4, the linkage sections 13 are configured such that the neighboring joint pieces 4 swivel about alternately non-parallel swivel axis lines S.

A guide plate 5 includes a disc-shaped first plate part 14 and a ring-shaped second plate part 15, which is attached to the outer circumference of the first plate part 14 such that the angle thereof can be adjusted in the circumferential direction.

Figure 7:
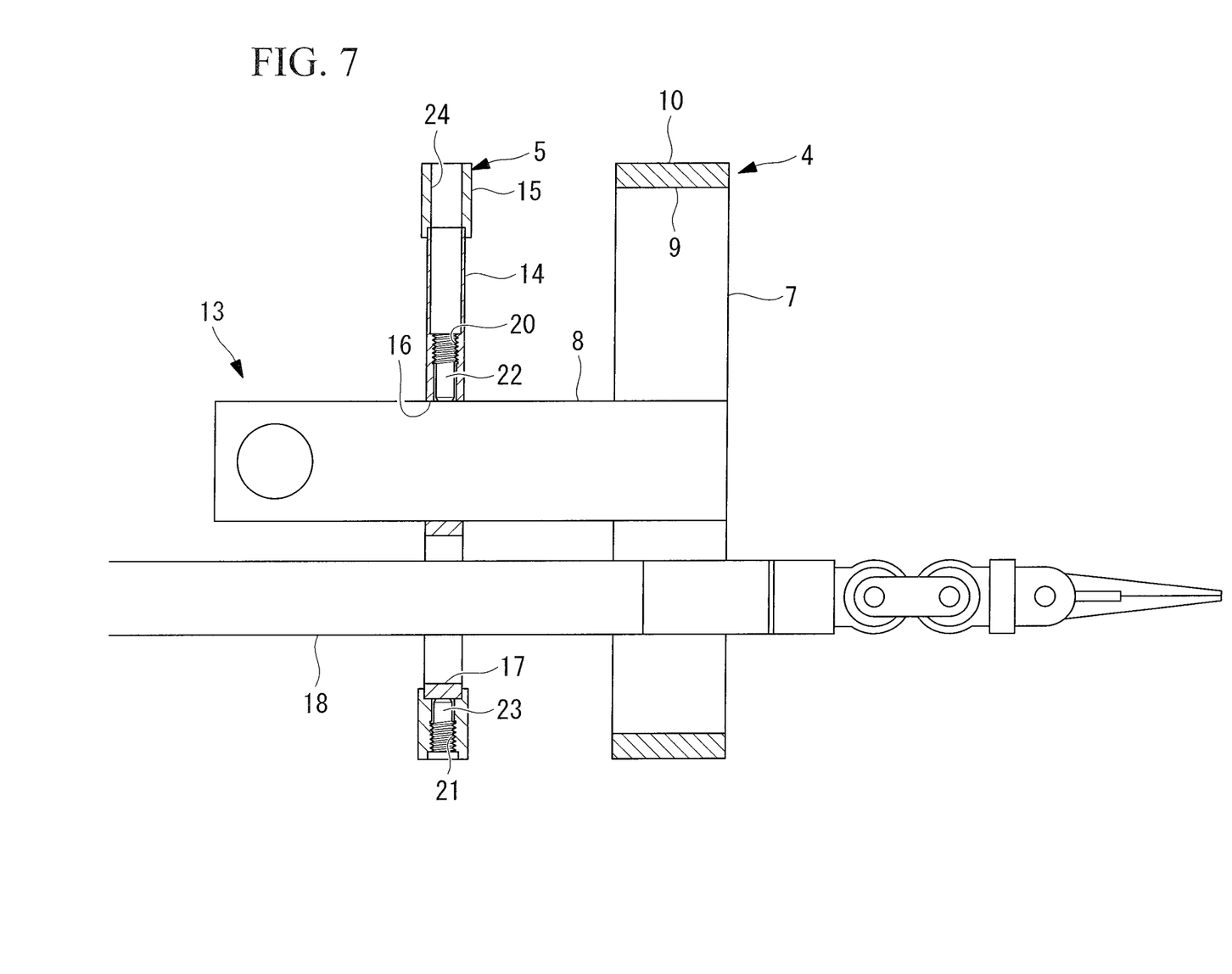
FIG. 7 is a longitudinal sectional view depicting a state in which a treatment tool is inserted through an opening in the bending mechanism in FIG. 3.

As shown in FIGS. 3 and 4, the first plate part 14 includes, at the center thereof, a fitting hole 16 into which the first columnar part 8 of a joint piece 4 is tightly fitted and also includes, outwardly from the fitting hole 16, four through-holes (openings) 17 passing therethrough in the plate-thickness direction. As shown in FIG. 7, the through-holes 17 are configured to allow a built-in device 18, like a flexible treatment tool, a pipe, or a flexible endoscope, to pass therethrough.

The second plate part 15 includes a plurality of through-holes (guide channels) 19 that are formed with a space therebetween in the circumferential direction and that pass therethrough in the plate-thickness direction. As shown in, for example, FIG. 5, these through-holes 19 are provided so as to be angled towards one circumferential direction relative to the direction parallel to the axis line of the second plate part 15. These through-holes 19 have a diameter larger than the external size of a sheath 26, serving as a component of a tension-transmissions 6 described later, and are formed so as to have dimensions large enough to allow the sheath 26 to pass therethrough. Chamfering or rounding processing is applied to the edges at both ends of each of the through-holes 19.

Figure 6:
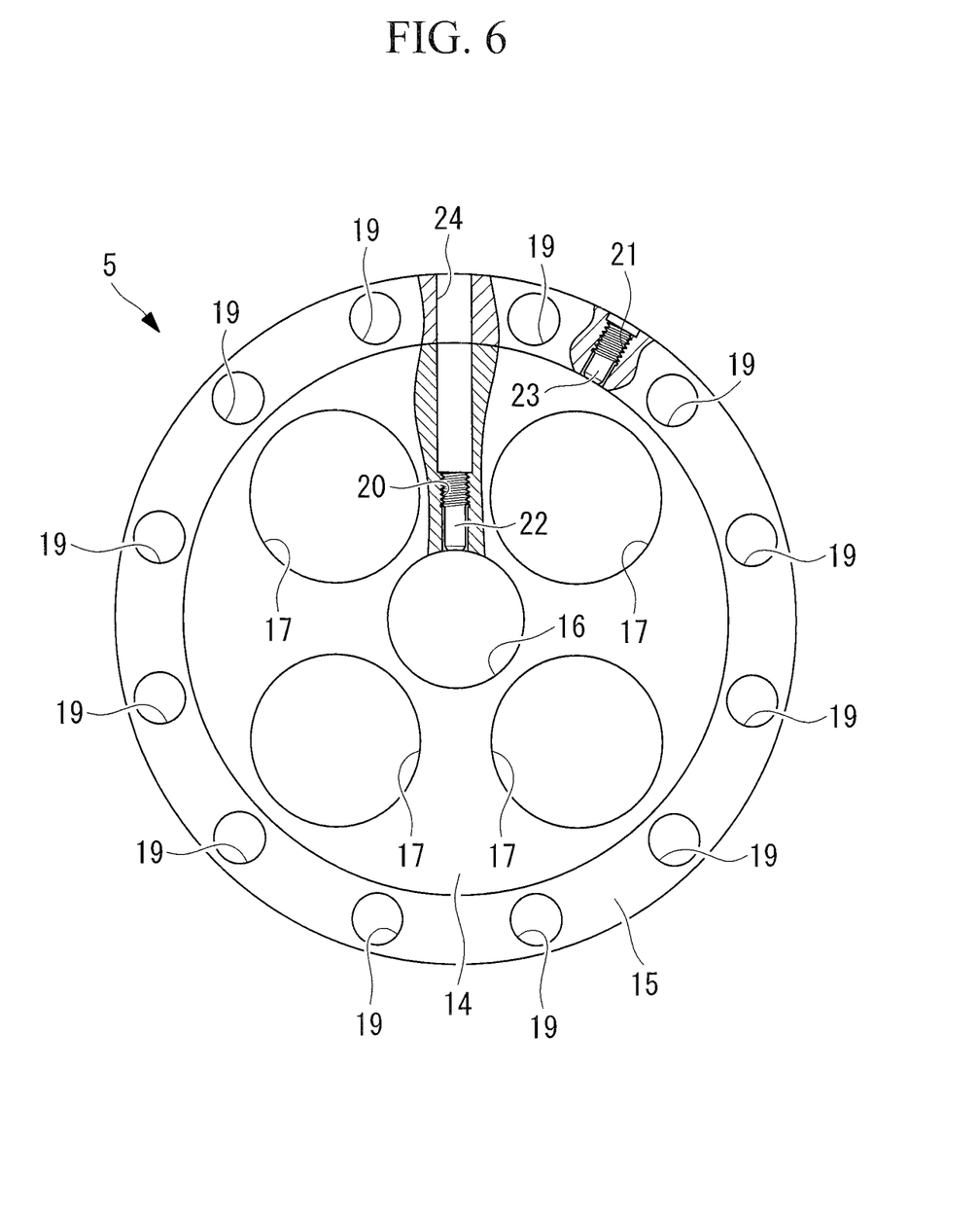
FIG. 6 is front elevational view of a partially cutaway of the guide plate in FIG. 4.

As shown in FIG. 6, the first plate part 14 and the second plate part 15 have screw holes 20 and 21 passing therethrough in the radial direction. Setscrews 22 and 23 are threaded into the screw holes 20 and 21, respectively. The first plate part 14 can be fixed to the first columnar part 8 by threading the setscrew 22 into the screw hole 20 in the first plate part 14 to press the setscrew 22 onto the outer surface of the first columnar part 8, which is tightly fitted into the fitting hole 16. The second plate part 15 can be fixed to the first plate part 14 by threading the setscrew 23 into the screw hole 21 in the second plate part 15 to press the setscrew 23 onto the outer surface of the first plate part 14.

In the example shown in FIG. 6, the second plate part 15 has a through-hole 24 passing therethrough in the radial direction, besides the screw hole 21. This through-hole 24 is formed at a predetermined angular position aligned with the screw hole 20 formed in the first plate part 14, namely, the predetermined angular position of the second plate part 15 relative to the first plate part 14. Because of this, in a state where the angular position of the second plate part 15 is adjusted relative to the first plate part 14 so that the through-hole 24 is aligned with the screw hole 20, the entire guide plate 5 can be positioned relative to the first columnar part 8 to thread the setscrew 22 into the screw hole 20, thus fixing the first plate part 14 to the first columnar part 8.

Figure 5:
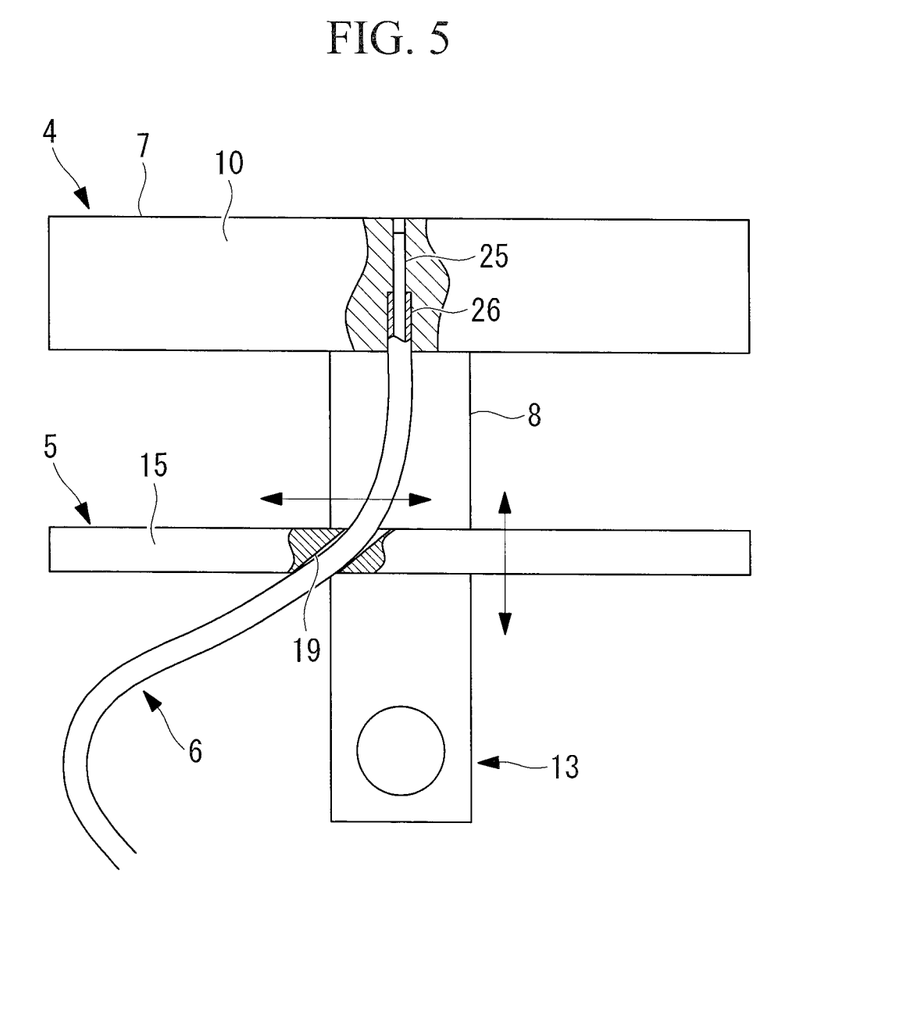
FIG. 5 is a side elevational view of a partially cutaway section of the bending mechanism in FIG. 3.

As shown in FIG. 5, a tension-transmissions 6 includes a wire 25 made of metal and the tubular sheath 26 covering that wire 25. A total of two tension-transmissions 6 are fixed to each of the joint pieces 4 at positions near the body part 7 with the first columnar part 8 therebetween, one at each of the positions on a plane that includes the axis line of the first columnar part 8 and that is orthogonal to the swivel axis line S. As shown in FIG. 3, when a tension F is applied to one of the tension-transmissions 6, the joint piece 4 and the guide plate 5 to which the tension-transmissions 6 is fixed are integrally swiveled about the swivel axis line S.

The sheath 26 is composed of a material with a low coefficient of friction, like tetrafluoroethylene, or alternatively, the outer surface of the sheath 26 is coated with such a material.

As shown in FIG. 2, each of the tension-transmissions 6 one end of which is fixed to the body part 7 of a particular joint piece 4 passes through a through-hole 19 in at least one guide plate 5 and through-holes 9 in the body parts 7 of the joint pieces 4 disposed towards the basal end side from the body part 7 of the particular joint piece 4 and is guided to the basal end side of the flexible medical apparatus 1.

Particularly in this embodiment, when the tension-transmissions 6 are made to pass through through-holes 19 in the plurality of guide plates 5 arranged with a space therebetween, they pass through through-holes 19 disposed at circumferential positions different from the positions of the through-holes 19 in the neighboring guide plates 5, whereby the tension-transmissions 6 are routed along spiral curved paths extending around the longitudinal axes of the joint pieces 4.

The operation of the flexible medical apparatus 1 and the bending mechanism 2 with the above-described structure according to this embodiment will be described below.

According to the bending mechanism 2 of this embodiment, when a tension is applied to one of the tension-transmissions 6 guided to the basal end side, the joint piece 4 to which one end of the tension-transmissions 6 that has received that tension is fixed is swiveled about the swivel axis line S, as shown in FIG. 3. By doing so, the position and the orientation of the distal end portion of the bending mechanism 2 can be changed.

In this case, even if one of the joint pieces 4 is swiveled, the tension-transmissions 6 for driving the other joint pieces 4 change only their curvature shapes and are prevented from changing their tensions since the tension-transmissions 6 are routed along spiral curved paths in the bending mechanism 2 according to this embodiment. Therefore, this affords an advantage in that the swivel angles of the other joint pieces 4 can be prevented from changing.

A tension-transmissions 6 is routed according to the procedures below. More specifically, the first columnar part 8 of a joint piece 4 is tightly fitted into the fitting hole 16 in a first plate part 14, and, without fixing the first plate part 14 to the first columnar part 8 with the setscrew 22, the tension-transmissions 6 is made to pass through a through-hole 19 in the second plate part 15. Thereafter, the position in the longitudinal-axis direction of the guide plate 5, the positions in the circumferential direction of the through-holes 17 in the first plate part 14, and the positions in the circumferential direction of the through-holes 19 in the second plate part 15 are adjusted. This position adjustment is performed so that all the tension-transmissions 6 can move smoothly.

The screw hole 20 in the first plate part 14 and the through-hole 24 in the second plate part 15 are aligned with each other in this state, and then a tool is inserted to thread the setscrew 22 into the screw hole 20 to fix the first plate part 14 to the first columnar part 8. By doing so, the positions in the circumferential direction of the through-holes 17 in the first plate part 14 and the position in the circumferential direction of the through-hole 19 in the second plate part 15 are fixed. Thereafter, the setscrew 23 is threaded into the screw hole 21 in the second plate part 15 to fix the second plate part 15 to the first plate part 14. The routing of the tension-transmissions 6 is completed by carrying out the above-described procedures on all the guide plates 5.

In this manner, according to the bending mechanism 2 of this embodiment, the routing of each of the tension-transmissions 6 along a curved path is achieved by making the tension-transmissions 6 pass through a through-hole 19 formed in the second plate part 15 of a guide plate 5. Thus, the position of the through-hole 19 in the circumferential direction can be adjusted by turning the second plate part 15 in the circumferential direction relative to the first plate part 14. Furthermore, the position in the longitudinal-axis direction of the through-hole 19 can also be adjusted by moving the first plate part 14 in the longitudinal-axis direction relative to the first columnar part 8 of the joint piece 4.

This affords an advantage in that the through-hole 19 can be arranged at a position at which the tension-transmissions 6 can be smoothly routed.

In this embodiment, because each of the guide plates 5 is divided into two parts so that the first plate part 14 and the second plate part 15 can rotate relative to each other, the circumferential positions of the through-holes 17 formed in the first plate part 14 and the circumferential positions of the through-holes 19 formed in the second plate part 15 can be adjusted independently of each other. In other words, there is an advantage in that the through-holes 19 in the second plate part 15 can be arranged at positions where the tension-transmissions 6 can be smoothly routed and in that the through-holes 17 in the first plate part 14 can be arranged at positions where the built-in device 18, like a treatment tool, can be made to pass through a through-hole 17 in a substantially straight line along the longitudinal axis.

Because the through-holes 19 in the second plate part 15 are formed so as to be angled towards the circumferential direction, the tension-transmissions 6 passing through a through-hole 19 can form a smooth curved path. Then, because the edges of each of the through-holes 19 are subjected to chamfering and so forth, the sheath 26 can be prevented from being caught by the edges when the sheath 26 moves in the through-hole 19. Furthermore, because the sheath 26 is formed of a material with a low coefficient of friction, like tetrafluoroethylene, the sheath 26 can be moved smoothly in the through-hole 19.

According to the flexible medical apparatus 1 of this embodiment, because the above-described bending mechanism 2 is covered with the flexible outer sheath 3, the outer sheath 3 prevents the bending mechanism 2 from coming into contact with body tissues when the bending mechanism 2 is inserted into the body, thereby protecting both the bending mechanism 2 and the body tissues. Then, because the bending mechanism 2 swivels only the intended joint piece 4 through the operation of one of the tension-transmissions 6, an advantage is afforded in that the distal end portion and so forth of the built-in device 18, like a treatment tool, disposed at the distal end of the bending mechanism 2 is prevented from moving in an unintended direction, thereby improving the operability.

Figure 8:
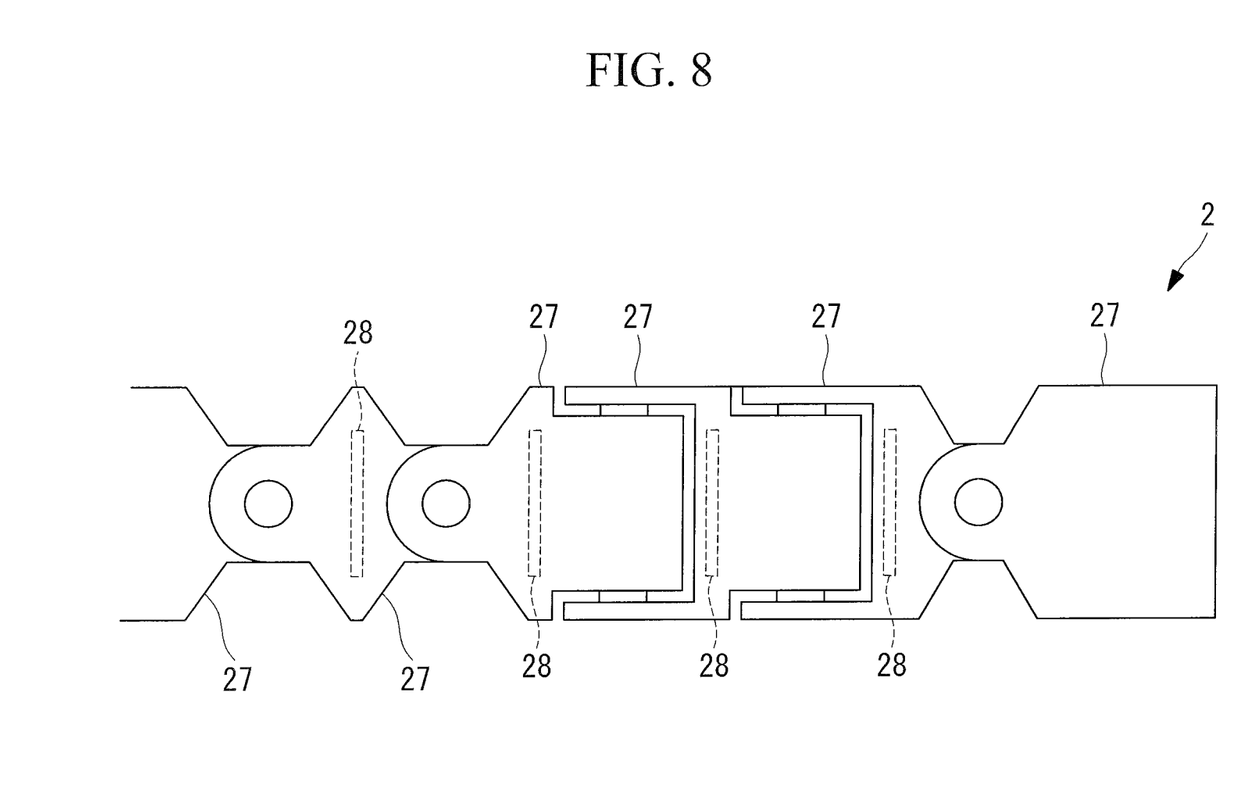
FIG. 8 is a schematic diagram depicting a modification of the bending mechanism in FIG. 2.

This embodiment has been described by way of an example of the joint pieces 4 having the first columnar parts 8 at the centers and the guide plates 5 having the fitting holes 16 into which the first columnar parts 8 are tightly fitted. Instead, cylindrical joint pieces 27 may be employed, as shown in FIGS. 8 and 9, and guide plates 28 the positions of which can be adjusted in the longitudinal direction and in the circumferential direction may be provided on the inner circumferential surfaces of the joint pieces 27.

Figure 9:
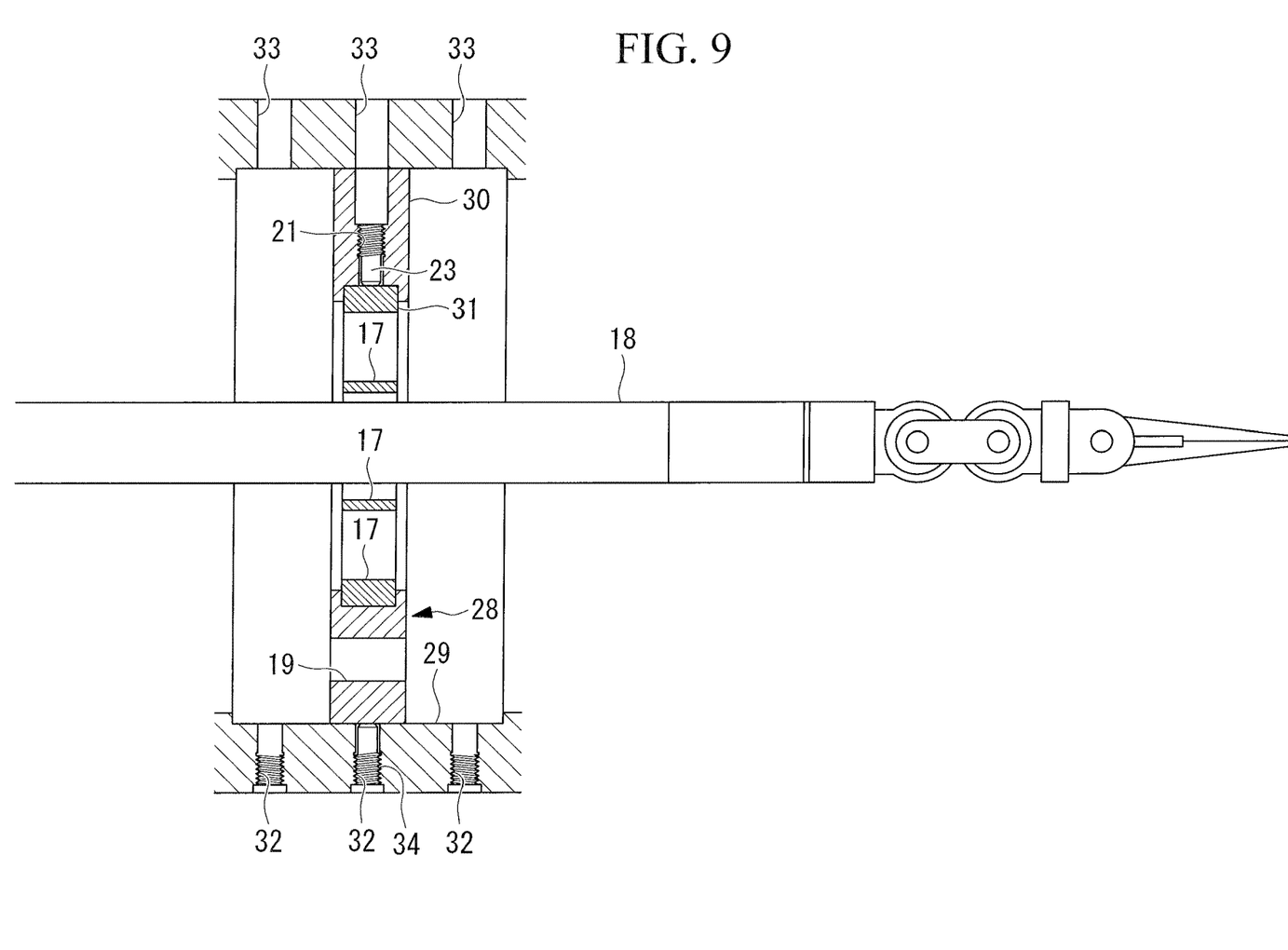
FIG. 9 is a longitudinal sectional view depicting a state in which a treatment tool is inserted through an opening in the bending mechanism in FIG. 8.

An example of the guide plates 28 is a guide plate, as shown in FIG. 9, that has: a ring-shaped second plate part 30 that is accommodated in a wide circumferential groove 29 formed on the inner circumferential surface of a joint piece 27 and that is disposed movably in the longitudinal-axis direction within the range of the width of that circumferential groove 29; and a first plate part 31 that is provided on the inner circumferential surface of the second plate part 30 so as to be able to move in the circumferential direction. This modification is the same as in the above-described embodiment in that the first plate part 31 has a through-hole 17 through which the built-in device 18 passes and in that the second plate part 30 has through-holes 19 through which the tension-transmissions (not shown in the FIG. 6 can pass.

In the example shown in the figure, three screw holes 32 and three through-holes 33 are formed at positions in the longitudinal-axis direction with a space therebetween so that the position of the guide plate 28 in the longitudinal-axis direction can be adjusted in three stages. The guide plate 28 can be fixed to the joint piece 27 by threading a setscrew 34 into the screw hole 32 in the joint piece 27 to press the setscrew 34 onto the outer surface of the second plate part 30.

In the description of this embodiment, three joint pieces 4 are used, as shown in FIG. 2. However, the number of joint pieces 4 is not limited to three. The number and size of the through-holes 17 and 19 provided in each of the guide plates 5 are not limited to those shown as examples in the drawings. Neighboring joint pieces 4 have been described as swiveling along swivel planes orthogonal to each other but are not limited to this. The angle at which the swivel planes intersect may be an angle other than 90°, and joint pieces 4 swiveling along the same swivel plane may be disposed adjacent to each other.

In the above-described embodiment, the tension-transmissions 6 have been described as being routed in the form of a helix. Instead, any curved shape that curves around the longitudinal axes of the joint pieces 4 may be employed.

As a result, the following aspect is read from the above described embodiment of the present invention.

One aspect of the present invention is a bending mechanism including: a plurality of bending joints connected in series along a longitudinal axis; a plurality of elongated tension-transmissions that transmit tensions for individually driving the bending joints; and at least one guide having guide channels that movably support the tension-transmissions in the longitudinal direction thereof and that guide the tension-transmissions along curved paths extending around the longitudinal axis.

According to this aspect, when a tension is applied to one of the tension-transmissions, the tension is transmitted to the bending joints to which the tension-transmissions is connected, and the bending joints swivels relative to a neighboring bending joints, whereby the position and orientation of the distal end portion of the bending mechanism can be changed. When a tension is applied to the tension-transmissions, which passes through a guide channel in the at least one guide and is guided along a curved path extending around the longitudinal axis, the tension-transmissions moves in the guide channel in the longitudinal direction so that the tension can be transmitted to the intended bending joints.

In this case, even if the tension is applied to the one tension-transmissions for swiveling the intended bending joints to swivel the intended bending joints, the curved paths of the tension-transmissions for swiveling the other bending joints change only in shape and are prevented from changing in length.

Consequently, only the intended bending joints can be swiveled without changing the tensions of the other tension-transmissions for swiveling the bending joints other than the intended bending joints to be swiveled, thus preventing the other bending joints from being swiveled unintentionally.

The guide may be a planar guide plate disposed so as to intersect the longitudinal axis, and the guide channels may be through-holes or through-grooves that pass through the guide plate in a plate-thickness direction.

By doing so, via the through-holes or through-grooves provided in the planar guide plate disposed so as to intersect the longitudinal axis, the tension-transmissions can be easily routed along the curved paths extending around the longitudinal axis.

The guide plate may be attached such that the angle thereof can be adjusted about the longitudinal axis.

By doing so, the guide plate can be rotated about the longitudinal axis, thereby making it possible to adjust the positions of the guide channels for forming the optimal curved paths of the tension-transmissions. Because of this, the tension-transmissions are prevented from taking an unnatural shape, thereby allowing the tension to be transmitted smoothly.

The guide plate may have, radially inward from the through-holes or the through-grooves, an opening that passes therethrough in the plate-thickness direction.

By doing so, a built-in device, such as a treatment tool or a pipe, can be guided from the basal end side to the distal end side of the bending mechanism through the opening.

The guide plate may include: a first plate part provided such that the angle thereof can be adjusted about the longitudinal axis relative to one of the bending joints; and a second plate part attached such that the angle thereof can be adjusted about the longitudinal axis relative to the first plate part, the opening may be provided in the first plate part, and the guide channels may be provided in the second plate part.

By doing so, when the positions of the guide channels are adjusted by rotating the first plate part about the longitudinal axis, the position of the opening can be set, regardless of the positions of the guide channels, by rotating the second plate part relative to the first plate part. In other words, the positions of the guide channels for optimizing the curved paths of the tension-transmissions and the position of the opening through which the built-in device is made to pass can be adjusted independently of each other.

The guide channels may be formed so as to be angled towards a circumferential direction relative to a direction parallel to the longitudinal axis.

By doing so, when spiral paths revolving around the longitudinal axis are set as the curved paths of the tension-transmissions, the spiral paths can also be formed smoothly in portions of the guide plate through which the tension-transmissions pass.

The tension-transmissions may be wires covered with sheaths.

By doing so, when a tension is applied to a wire that is smoothly routed via a guide channel in the guide plate, the tension can be smoothly transmitted to the intended bending joints because the sheath moves relative to the guide channel.

The surfaces of the sheaths and the inner walls of the guide channels may be composed of different materials.

By doing so, even if the tension applied to a wire causes the surface of the sheath to come into close contact with the inner walls of the guide channels, it is possible to prevent the surface of the sheath from firmly sticking to the inner walls of the guide channels, thereby ensuring smooth movement.

A coating for decreasing the friction with the inner walls of the guide channels may be applied to the surfaces of the sheaths.

By doing so, the friction is reduced due to the coating even if the tension applied to a wire causes the surface of the sheath to come into close contact with the inner walls of the guide channels, thus ensuring smooth movement of the tension-transmissions.

Another aspect of the present invention is a flexible medical apparatus including: one of the above-described bending mechanisms; and a flexible tubular outer sheath covering the outer circumference of the bending mechanism.

By covering the bending mechanism with the outer sheath, the bending mechanism is prevented from coming into direct contact with tissues in the body even when it is inserted into the body, thereby protecting tissues and the bending mechanism and also ensuring smooth movement of the bending mechanism.

REFERENCE SIGNS LIST

1 Flexible medical apparatus
2 Bending mechanism
3 Outer sheath
4 Joint pieces (bending joints)
5 Guide plate (guide)
6 Tension-transmissions
9 Through-hole
14 First plate part
15 Second plate part
17 Through-hole (opening)
19 Through-hole (guide channel)
25 Wire
26 Sheath

The invention claimed is:

1. A bending mechanism comprising:
a plurality of bending joints arranged to extend in a longitudinal direction, the plurality of bending joints being bendably articulated relative to each other; and
a plurality of wires configured to transmit tension for individually articulating the plurality of bending joints,
wherein each of the plurality of bending joints having:
a joint piece through which the plurality of wires pass;
a column extending in the direction of a longitudinal axis from a center of the joint piece; and
a guide connected to each of the plurality of bending joints by fixing a center of the guide with the column, the guide having guide channels configured to guide the plurality of wires in the longitudinal direction, and
wherein the joint piece from each of the plurality of bending joints does not articulate relative to a corresponding one of the guides in a same bending joint; and
one or more of the plurality of wires forms a spiral path extending around the longitudinal axis.

2. The bending mechanism according to claim 1, wherein the guide is a planar guide plate disposed so as to intersect the longitudinal axis, and
the guide channels are through-holes or through-grooves that pass through the guide plate in a plate-thickness direction.

3. The bending mechanism according to claim 2, wherein the guide plate is attached such that the angle thereof can be adjusted about the longitudinal axis.

4. The bending mechanism according to claim 2, wherein the guide plate has, radially inward from the through-holes or the through-grooves, an opening that passes therethrough in the plate-thickness direction.

5. The bending mechanism according to claim 3,
wherein the guide plate includes: a first plate part provided such that the angle thereof can be adjusted about the longitudinal axis relative to one of the plurality of bending joints; and a second plate part attached such that the angle thereof can be adjusted about the longitudinal axis relative to the first plate part,
the opening is provided in the first plate part, and
the guide channels are provided in the second plate part.

6. The bending mechanism according to claim 2, wherein the guide plate is attached such that the position thereof can be adjusted in a longitudinal-axis direction relative to the plurality of bending joints.

7. The bending mechanism according to claim 2, wherein the guide channels are formed so as to be angled towards a circumferential direction relative to a direction parallel to the plate-thickness direction.

8. The bending mechanism according to claim 1, wherein the plurality of wires are moveably covered with sheaths.

9. The bending mechanism according to claim 8, wherein the surfaces of the sheaths and inner walls of the guide channels are composed of different materials.

10. The bending mechanism according to claim 9, wherein a coating for decreasing the friction with the inner walls of the guide channels is applied to the surfaces of the sheaths.

11. A medical apparatus comprising:
an insertion section; and
a bending mechanism provided with the insertion section, wherein the bending mechanism including:
a plurality of bending joints arranged to extend in a longitudinal direction, the plurality of bending joints being bendably articulated relative to each other; and
a plurality of wires configured to transmit tension for individually articulating the plurality of bending joints,
wherein, each of the plurality of bending joints having:
a joint piece through which the plurality of wires pass;
a column extending in the direction of a longitudinal axis from a center of the joint piece; and
a guide connected to each of the plurality of bending joints by fixing a center of the guide with the column, the guide having guide channels configured to guide the plurality of wires in the longitudinal direction, and
wherein the joint piece from each of the plurality of bending joints does not articulate relative to a corresponding one of the guides in a same bending joint; and
one or more of the wires forms a spiral path extending around the longitudinal axis.

12. The medical apparatus according to claim 11, further comprising a flexible tubular outer sheath covering the outer circumference of the bending mechanism.

13. The medical apparatus according to claim 11,
wherein the guide is a planar guide plate disposed so as to intersect the longitudinal axis, and
the guide channels are through-holes or through-grooves that pass through the guide plate in a plate-thickness direction.

14. The medical apparatus according to claim 13, wherein the guide plate is attached such that the angle thereof can be adjusted about the longitudinal axis.

15. The medical apparatus according to claim 13, wherein the guide plate has, radially inward from the through-holes or the through-grooves, an opening that passes therethrough in the plate-thickness direction.

16. The medical apparatus according to claim 14,
wherein the guide plate includes: a first plate part provided such that the angle thereof can be adjusted about the longitudinal axis relative to one of the plurality of bending joints; and a second plate part attached such that the angle thereof can be adjusted about the longitudinal axis relative to the first plate part,
the opening is provided in the first plate part, and
the guide channels are provided in the second plate part.

17. The medical apparatus according to claim 13, wherein the guide plate is attached such that the position thereof can be adjusted in a longitudinal-axis direction relative to the plurality of bending joints.

18. The medical apparatus according to claim 13, wherein the guide channels are formed so as to be angled towards a circumferential direction relative to a direction parallel to the plate-thickness direction.

19. The medical apparatus according to claim 11, wherein the plurality of wires are moveably covered with sheaths.

20. The medical apparatus according to claim 19, wherein the surfaces of the sheaths and inner walls of the guide channels are composed of different materials.

* * * * *